United States Patent [19]
Daly et al.

[11] Patent Number: 5,356,383
[45] Date of Patent: Oct. 18, 1994

[54] HYPODERMIC NEEDLE/SYRINGE ASSEMBLIES AND DEVICE FOR REMOVING NEEDLES THEREFROM

[75] Inventors: Eugene Daly, Cork; Owen McAuliffe, County Cork, both of Ireland

[73] Assignee: Damal Limited, Cork, Ireland

[21] Appl. No.: 653,421

[22] Filed: Feb. 11, 1991

[30] Foreign Application Priority Data

| Feb. 9, 1990 [IE] | Ireland | 465/90 |
| Apr. 27, 1990 [IE] | Ireland | 1512/90 |
| Jun. 19, 1990 [IE] | Ireland | 2204/90 |

[51] Int. Cl.⁵ ............................................. A61W 5/00
[52] U.S. Cl. ................................. 604/110; 206/366; 206/369
[58] Field of Search .............. 604/110, 263, 266, 282, 604/240, 192, 199; 206/363-370, 635, 380, 438

[56] References Cited

U.S. PATENT DOCUMENTS

| 2,953,243 | 9/1960 | Roehr | 604/263 |
| 3,021,942 | 2/1962 | Hamilton | 604/192 |
| 3,036,700 | 5/1962 | Krug | 206/365 |
| 3,114,455 | 12/1963 | Claisse et al. | 206/366 |
| 3,390,759 | 7/1968 | Vanderbeck | 206/365 |
| 4,248,246 | 2/1981 | Ikeda | 604/263 |
| 4,740,205 | 4/1988 | Seltzer et al. | 604/192 |
| 4,862,573 | 9/1989 | Kelson et al. | |
| 4,973,315 | 11/1990 | Sincock | 604/263 |
| 5,002,536 | 3/1991 | Thompson et al. | 604/192 |

FOREIGN PATENT DOCUMENTS

| 0261513 | 3/1988 | European Pat. Off. |
| 0304619 | 3/1989 | European Pat. Off. |
| 0309965 | 4/1989 | European Pat. Off. |
| 1383905 | 2/1975 | United Kingdom |
| 8806133 | 8/1988 | World Int. Prop. O. |

Primary Examiner—John D. Yasko
Assistant Examiner—Ronald K. Stright, Jr.
Attorney, Agent, or Firm—Young & Thompson

[57] ABSTRACT

A removal device for removing a hypodermic needle assembly from a syringe, wherein the removal device comprises a sleeve provided internally with a series of ribs which engage with a series of ribs on the needle assembly, or on an attachment adaptor on the needle assembly, when the sleeve is rotated to unscrew the needle assembly from the syringe, the sleeve having a clear passage therethrough and having an internal diameter such that the needle assembly and adaptor thereon (if present) can pass freely through it in an axial direction. The sleeve is removably engageable in a hollow shaft through which the needle assembly and adaptor (if present) can drop to a "sharps" container below. The shaft is integrally formed and is power-driven through a gear formation on its external surface. A manually-operated device is also described, having a fixed sleeve as described above in which the needle assembly is held while the syringe is unscrewed from it. A preferred syringe has an open end through which the cartridge can drop when the needle assembly is unscrewed from the syringe. The needle hub or adaptor has a skirt which is internally screw-threaded to engage the front end of the syringe. The front end of the cartridge lies within the skirt. A removal device for conventional syringes and conventional needle assemblies is also described.

4 Claims, 13 Drawing Sheets

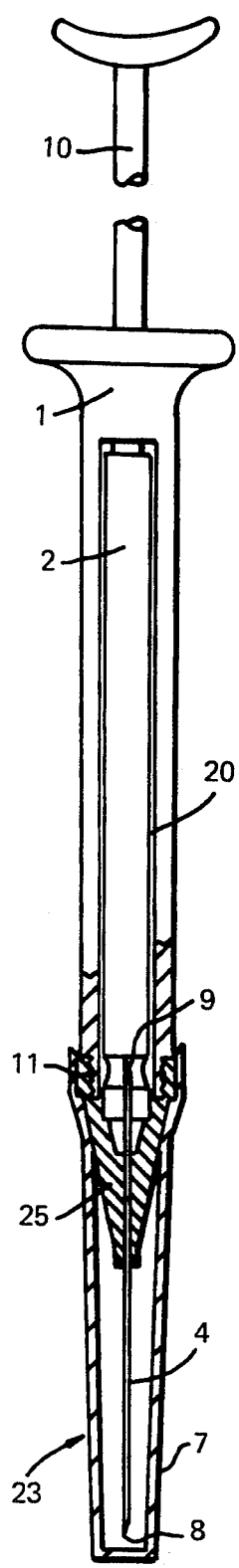
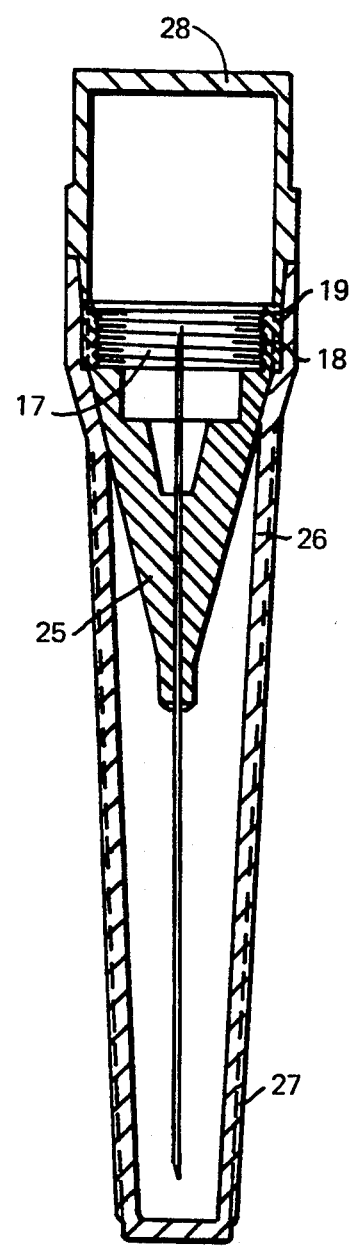
FIG. 5a  FIG. 6a

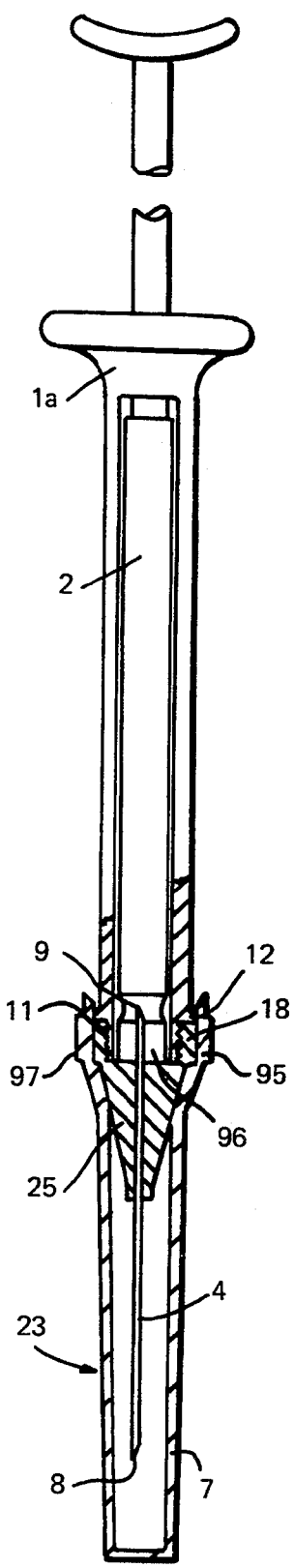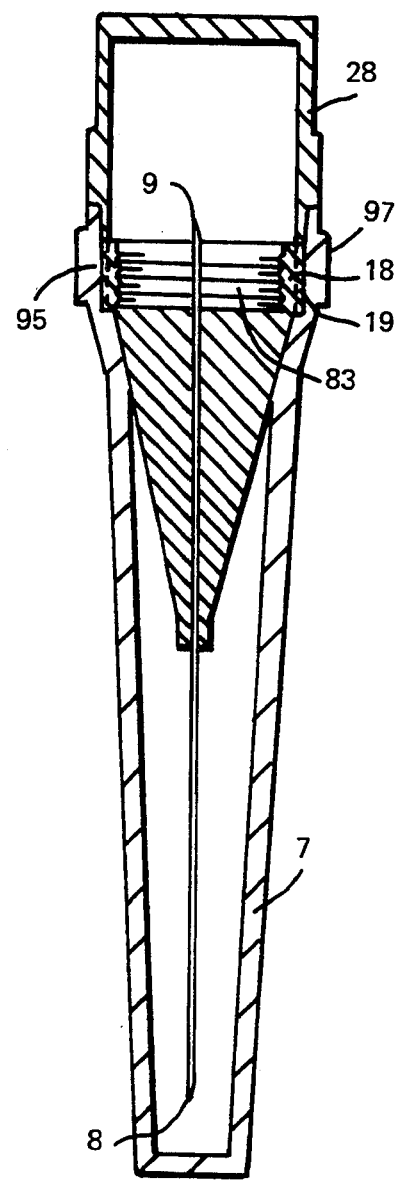
FIG. 5b
FIG. 6b

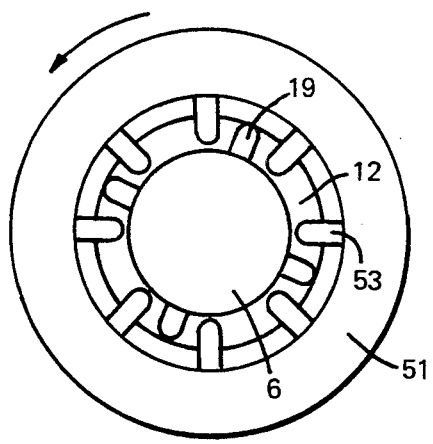
FIG. 12
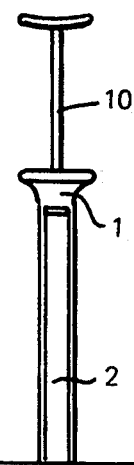
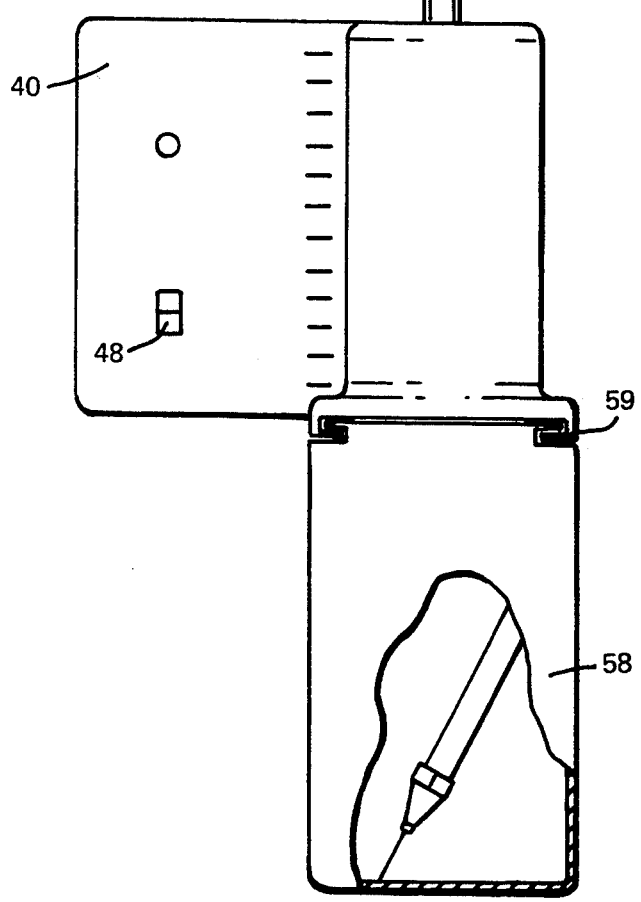
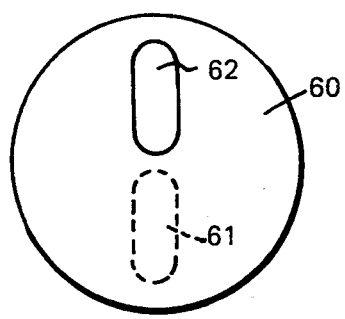
FIG. 14  FIG. 13

5,356,383

HYPODERMIC NEEDLE/SYRINGE ASSEMBLIES AND DEVICE FOR REMOVING NEEDLES THEREFROM

BACKGROUND OF THE INVENTION a) Field of the Invention

This invention relates to hypodermic needle/syringe assemblies and to a device for removing needles therefrom. It is more particularly concerned with needle/syringe assemblies used for injection of anesthetics in dental practice but it also has applicability in other fields of human and veterinary medicine.

b) Description of the Related Art

There is increasing concern about the dangers of infection arising from the use of hypodermic needles, particularly because of the health risks associated with diseases such as AIDS and Hepatitis B. Various devices have been proposed for the disposal of used needles. WO 88/06133 Bruno acknowledges a number of prior art disposal devices including one sold under the name "SHARPS—tainer" in the USA which comprises a jar-like container with a snap-on lid to which is mounted a plier-like device for grasping a needle hub and unscrewing it from the syringe. Bruno describes a needle removal and storage device which includes a manually-squeezable grasping device having opposed jaw-like segments to grasp the needle hub. CA 1,184,547 Frontier Plastics (South Wales) Limited describes a disposal bin having a top wall provided with a keyhole slot in which the needle can be engaged for removal from the syringe. EP 0,261,513 Bauer describes a similar device having a dumb-bell shaped slot in its top cover. Other removal devices are shown in GB 2,205,043A Jones et. al., GB 2,215,215A Snow Brand Milk Products Limited and EP 0,309,965A2 Nissho Corporation.

There is a known needle safety device which is illustrated in "Dental Update", March 1989, page 63. This device comprises a tapering sleeve having a hexagonal internal surface, and a broad hexagonal flange extending radially from the wider end of the sleeve and acting as a needle guard. When an operator is preparing to use a needle, he/she inserts the needle sheath into the sleeve of the safety device so that it becomes engaged therein. After the needle has been used, the operator can hold the device by the broad flange and reinsert the needle back into the sheath. By gripping the flange, the operator can then unscrew the needle/sheath assembly from the syringe. Subsequently the operator can press against the closed end of the sheath to make the needle/sheath assembly slide out of the safety device and fall into a disposal bin. However there is still a risk of needle-stick injuries with this device, particularly when the needle is being re-inserted into the sheath.

Another known device called "ON-GARD Recapper" sold by ON-GARD Systems Inc of Denver, Colo., U.S.A. comprises a broad flange at one end of a sleeve which incorporates a manually-operable gripping mechanism. When an actuator or the sleeve is depressed, a needle sheath can be inserted into the sleeve. The actuator is then released and the sheath is held by the gripping mechanism. The device is used in a manner similar to that described in the preceding paragraph, the actuator being released finally to transfer the used needle/sheath assembly to a disposal bin.

A further known device called "DisposiNeedle from Septodont" marketed by Deproco U.K. Limited, Maidstone, Kent, England comprises a needle guard, an oval sleeve incorporating a trigger mechanism, and a "sharps" container. After a needle/sheath combination has been screwed into the end of a dental syringe by hand, the sheath is inserted through the needle guard into the sleeve, the trigger mechanism being squeezed to permit entry of the sheath. The trigger mechanism is then released to grip the sheath. After use of the needle and syringe, the needle is replaced into the sheath. The dentist then unscrews the syringe from the needle with one hand while holding the "DisposiNeedle" device in the other hand. After the syringe has been disengaged, the trigger mechanism is activated again to allow the needle/sheath assembly to drop into the "sharps" container. Alternatively, the "DisposiNeedle" device can be used to remove a needle from a syringe without any sheath present.

U.S. Pat. No. 4,798,587 Willoughby describes a device comprising releasable gripping means for releasably gripping the needle and a drive mechanism for rotating the needle when gripped by the gripping means, the gripping means being designed so that the needle can move freely away from the gripping mechanism when released. The drive mechanism may be electric driven or manually operable. The releasable gripping means includes a pivotable lever for bringing one or more wheels and/or a rack into engagement with the needle hub in order to rotate it, and then for disengaging from the needle so that it can fall into a container.

Conventional hypodermic needles comprise a cannula having front and rear points, and a hub secured to the cannula. The hub generally has a body with a gripping surface which may suitably be octagonal or other non-cylindrical shape, and an annular shoulder which is of greater diameter than the gripping surface and which is located rearwardly of the gripping surface, i.e. nearer to the rear point of the cannula. This means that if the needle/syringe assembly is inserted into a gripping device such as a keyhole slot with the front point of the cannula pointing downwardly, and the syringe is then removed, the shoulder on the hub prevents the needle from falling into the container below, unless the needle is moved, which involves a risk of contaminating contact. Likewise with squeezable gripping means of the type described by Bruno or Willoughby or as in the "ON-GARD Recapper" and "DisposiNeedle" devices, it is necessary to move the gripping means apart before the needle can fall down into the container. As a result the needle comes into contact with movable or mechanical parts of the device, which may become contaminated and will be difficult to clean and sterilize.

There is an additional risk of disease being spread through the use of conventional syringes. Such syringes, particularly as used in dental practice, generally have a closed cap portion at each end, the rear cap having a hole for passage of the plunger, and the front cap having a hole for entry of the inner end of the cannula. A cartridge of anesthetic is inserted through a long slot in the barrel of the syringe and the rear point of the cannula pierces a rubber diaphragm at the front end of the cartridge. The hole at the front end of the syringe is generally of small diameter and there is a risk that the wall defining the hole may be contaminated as the rear point of one needle is withdrawn through it and thus contamination may be transferred to a fresh needle as it is being inserted into the syringe.

Contamination of the rear point of the needle may arise from body fluids such as blood being sucked up the needle, particularly in the course of "aspiration". Aspiration is a test carried out, particularly in dental practice, in order to ascertain whether the outer point of the needle has been inserted into a blood vessel. Gentle pressure is applied to the anesthetic in the cartridge and then this pressure is released; if the needle has been inserted into a blood vessel, blood will be sucked up the needle into the cartridge and will be visible there. When the needle is subsequently withdrawn from the cartridge after use, the exterior of the rubber diaphragm at the base of the cartridge may also become contaminated. This means that there is a potential health risk in handling the cartridges after use. Conventionally, cartridges are withdrawn through the slot in the syringe wall and disposed of separately from the needles.

GB 1,383,905 Amalgamated Dental Co. Ltd. describes a needle/cartridge/syringe assembly in which the syringe barrel is open at its front end but is internally screw-threaded while the hub of the needle has a skirt which can be introduced into the lower end of the barrel and engaged therein in screw-threaded relationship. The cartridge can pass in and out through the front end of the barrel. In use, the needle is assembled into the cartridge before the latter is inserted into the barrel of the syringe. After administering the injection, the needle and cartridge are removed from the syringe as one unit. No device for removing the needle/cartridge assembly is described. The needle hub as shown in the drawings of this specification also has a shoulder rearwardly of its gripping surface which would prevent the needle/cartridge assembly from falling into the container of a disposal device as described above. So far as the present Applicants are aware, the assembly of GB 1,383,905 has not been commercialized.

A known form of dental syringe has an open front end with an internally screw-threaded metal cap which is screw fitted onto external screw threads on the syringe. The cap has a boss for attachment of a needle assembly. Its circumference is knurled for improving manual gripping. It is a permanent part of the syringe unit and is not disposable.

U.S. Pat. No. 4,740,205 Seltzer et al describes a disposable needle system for receiving/dispensing fluids such as body fluids, medicaments, vaccines and the like. The needle is provided with a threaded plastic hub which is designed to be screwed into an aperture in the front wall of a tube holder. The tube holder is adapted to receive and support a tube or container for fluid. A sleeve rotatably mounted on the forward end of the tube holder comprises a socket-wrench-like device for rotating the needle hub to release the needle from the tube holder after use without requiring any human contact with the needle itself. A disc portion of the needle hub, which has an outer diameter greater than that of any other portion of the hub, is provided with radially outwardly extending drive arm elements for engagement with the wrench-like sleeve.

The drive arm elements fit into longitudinally extending drive slots formed in the front end of the socket wall. The sleeve does not have any internal configuration for engaging the needle hub. The drive arm elements on the disc portion of the hub do not fit inside the sleeve.

The system of Seltzer et al is not designed for use with a syringe. The wrench-like sleeve would be particularly awkward to accommodate on a dental syringe. Seltzer makes no provision for disengaging the rear point of the needle from the diaphragm of a cartridge of anaesthetic or the like. Due to frictional contact between the needle and the diaphragm, the needle would not be free to drop away from the tube holder after unscrewing of the hub, as described by Seltzer at column 7 lines 1–3 and lines 45–48. Allowing a used needle to drop downwardly into an awaiting receptacle involves a risk that the needle will fall outside the receptacle and may then have to be handled manually.

It is an object of the present invention to improve the needle/syringe assemblies which are commercially available and to provide a new and inventive disposal device.

SUMMARY OF THE INVENTION

The present invention provides a removal device for removing a hypodermic needle assembly from a syringe, wherein the removal device comprises a sleeve provided with an internal engagement configuration engageable with an external engagement configuration on the needle assembly or on an attachment adaptor therefor, the sleeve having a clear passage therethrough and having an internal diameter such that the needle assembly and adaptor therefor (if present) can pass freely through it in an axial direction but the respective engagement configurations engage together during rotational movement of the sleeve relative to the syringe about the axis of the sleeve. The engagement configuration on the sleeve is a fixed feature of the sleeve and does not involve any moveable gripping means.

In a particular preferred embodiment, the internal engagement configuration on the sleeve comprises a series of ribs aligned parallel to the axis, the ribs meshing together with the external engagement configuration on the needle assembly or attachment adaptor thereon (if present). Preferably there are up to 8 ribs spaced around the internal circumference of the sleeve and projecting from the internal surface by about 0.3–0.75 mm, preferably about 0.45–0.55 mm.

Preferably the sleeve is removably engageable in or forms part of a hollow shaft through which the needle assembly and adaptor (if present) can pass freely in an axial direction, and drive means are provided externally of the shaft for rotating it about its axis. Most preferably, the hollow shaft is integrally formed so that infected fluids or washing water passing through the shaft cannot gain access to the drive means. In the preferred embodiments, the sleeve is removable from the shaft for autoclaving or sterilization.

Preferably the internal diameter of the sleeve is such that a cartridge from the syringe can pass through the sleeve with the needle assembly. More preferably the internal diameter is such that the syringe cannot pass the internal engagement configuration on the sleeve.

In one form of removal device according to the invention, particularly for use with conventional needle assemblies, the engagement configuration on the sleeve comprises a top portion defining a slot having a narrow portion on the axis of the sleeve and at least one wider part offset from the axis, such that the engagement configuration of a needle assembly is engageable in the narrow portion but the needle assembly can pass through the wider part after movement sidewardly in the slot. Preferably the top portion of the sleeve defining the slot has inclined lower surfaces for separating the needle assembly from the syringe in an axial direction during sidewards movement of the needle assembly in the slot.

According to one aspect, the present invention provides a hypodermic needle assembly attachable to a syringe, or an attachment adaptor of plastics material therefor, wherein the body of the needle hub or adaptor therefor has an external engagement configuration engageable with a device for rotating said needle assembly or adaptor about its axis, and has a rearwardly-open recess to receive the front end of a cartridge of fluid.

Preferably the engagement configuration comprises a series of ridges parallel to the axis provided on the part of the needle assembly or adaptor which is of greatest diameter. A series of 4 equiangularly spaced ridges is preferred but the series may obviously have half or double this number of ridges with equivalent effect.

In one embodiment said ridges are formed by ribs standing proud of a cylindrical surface, e.g. projecting from said surface by about 0.3–0.75 mm, preferably about 0.45–0.55 mm.

In another embodiment, said ridges are formed by intersecting faces of a polygonal surface.

Preferably the ridges are formed on the external surface of a cylindrical skirt extending rearwardly from the needle hub or adaptor therefor.

Most preferably, the skirt is internally configured for engagement with the front end of a syringe.

According to one feature, the present invention provides a hypodermic needle assembly having a scabbard whose rearward edge lies rearwardly of the rear point of the needle when the scabbard is in position on the needle assembly. In one embodiment, the rear point of the needle extends rearwardly of the needle hub but not beyond the rear edge of the scabbard.

According to a further feature, the invention provides a needle assembly having a scabbard wherein the portion of the scabbard having the greatest diameter has an engagement configuration engageable with a device for rotating the needle assembly about its axis, the engagement configuration preferably comprising a series of ridges, more preferably ribs, parallel to the axis.

According to another feature, the present invention provides an attachment adaptor for a needle assembly, wherein the front end of the adaptor is externally configured for engagement with the rear of a needle hub.

According to a further feature, the present invention provides a syringe for use with a needle assembly or adaptor as described above wherein the front end of the syringe barrel is open, the front end portion of the syringe barrel is circumferentially configured for engagement with the needle assembly or adaptor, and the syringe barrel has a radially projecting shoulder behind said front end portion, the shoulder having a diameter such that it will not pass the internal engagement configuration of the sleeve of a removal device as described above.

In yet another feature, the present invention provides a stand for a needle/syringe assembly wherein a holder for a scabbard is provided, spaced from a rest for the syringe. Preferably the scabbard holder is provided with a tapered hole to receive the scabbard.

BRIEF DESCRIPTION OF THE INVENTION

The invention is illustrated by way of Example in the following drawings, in which:

FIG. 3 shows an alternative embodiment of the adaptor similar to FIG. 2a;

FIG. 5a is an elevation partly in cross section of a second embodiment of a needle/syringe assembly in accordance with the invention;

FIG. 6a is an enlarged vertical cross section (similar to FIG. 2a) of the needle of FIG. 5a together with a protective cap;

FIGS. 5b and 6b are corresponding views of a variation of the second embodiment;

FIG. 12 is a diagrammatic horizontal sectional view from below illustrating the engagement between the needle or adaptor and the removal device, the ribs on both the sleeve and the needle or adaptor being enlarged for purposes of clarification;

FIG. 13 is a diagrammatic elevation, partly cut away, of the removal device of FIG. 11 in use with a "sharps" container beneath it;

FIG. 14 is a plan view of a cover for the "sharps" container in the device of FIG. 13;

Figure 27:
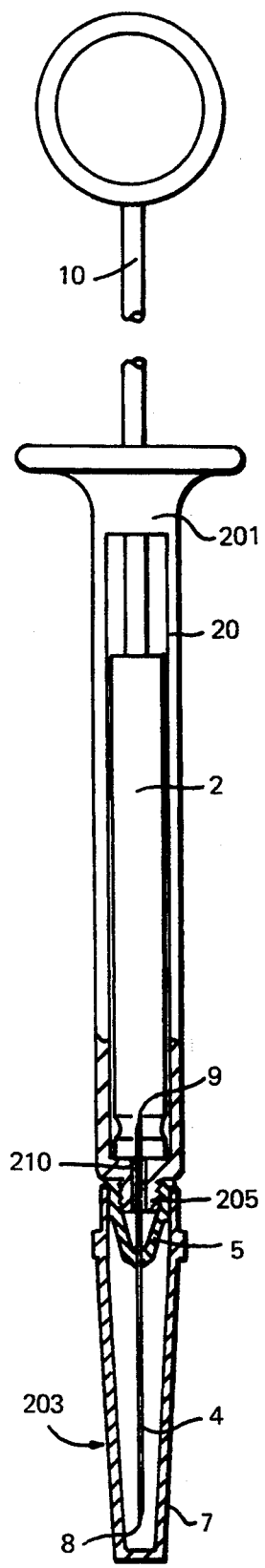
FIG. 27 is an elevation, partly in cross section, of a conventional needle/syringe assembly.
Figure 29:
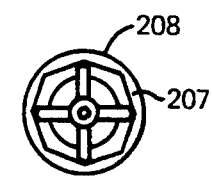
FIG. 29 is an underneath plan view of the needle of FIG. 28.
Figure 28:
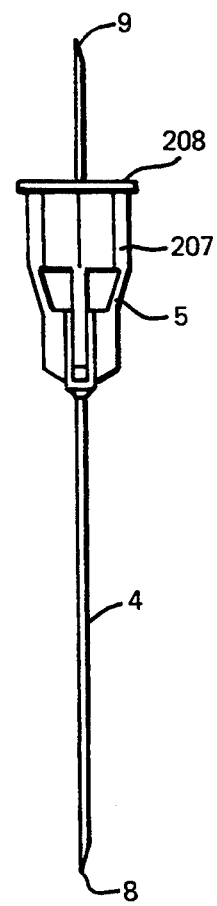
FIG. 28 is an enlarged vertical elevation of the needle of FIG. 27.

As shown in FIGS. 27-29 (Prior Art), a conventional needle/syringe assembly comprises a dental syringe 201, an anaesthetic cartridge 2 and a needle assembly 203. The needle assembly comprises a cannula 4 secured in a needle hub 5. The needle is screw-threadly joined to a threaded boss 205 at the front end of the syringe. The needle assembly shown in FIG. 27 also has a scabbard 7, which protects the front or injection point 8 of the cannula. The rear point 9 of the cannula has pierced the rubber diaphragm 96 at the front end of the anaesthetic cartridge.

The syringe 201 is closed at the rear end but has a hole (not shown) to permit passage of a conventional plunger 10. The plunger acts against a slidable rubber stopper (not shown) at the rear end of the cartridge.

A conventional needle hub 5 as shown in FIGS. 28 and 29 comprises a body having a gripping surface 207 which may be octagonal or some other non-cylindrical shape which facilitates the ease of assembly of the needle to the syringe. The needle also has an annular shoulder 208 of greater diameter than the gripping surface and located rearwardly of the gripping surface (i.e. nearer to the rear point 9 of the cannula). This annular shoulder prevents the needle dropping by gravity if inserted into a device such as a keyhole slot, unless the needle is moved. Likewise, when using a removal device as described by Bruno or Willoughby, it is necessary to move the gripping means apart before the needle can fall freely into a container.

In use, a dentist takes a syringe 201 and screws a conventional needle assembly 203 onto the thread 205 on the end of the syringe. The rear point 9 of the cannula passes through a hole 210 in the front end of the syringe. The dentist then loads an anaesthetic cartridge 2 into the syringe through a slot 20 in the side of the syringe. By pushing the cartridge forward, the rubber diaphragm at the front end of the cartridge is pierced by the rear point 9 of the cannula. Alternatively, the cartridge may be placed in the barrel of the syringe before the needle assembly is screwed onto the syringe.

After use the dentist can either remove the cartridge first and then the needle, or the needle first and then the cartridge. Either way, there is a problem with the present methods.

DESCRIPTION OF THE PREFERRED EMBODIMENTS

Figure 1:
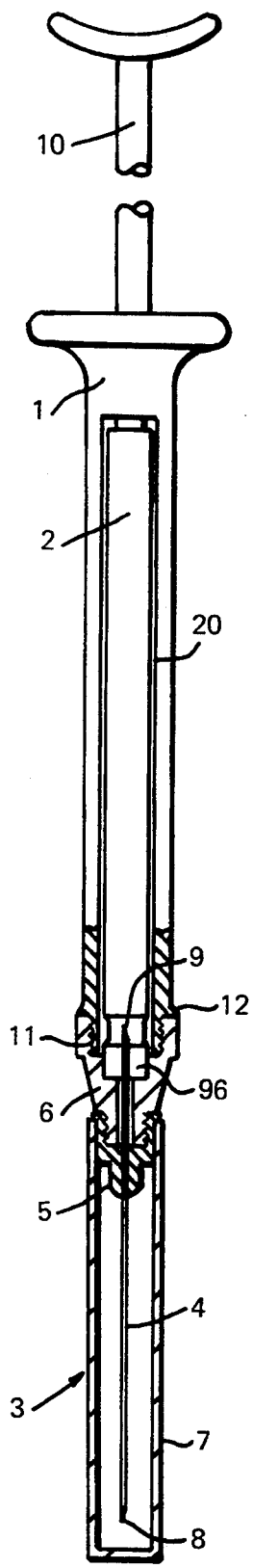
FIG. 1 is an elevation, partly in cross section, of a first embodiment of a needle/syringe assembly in accordance with the invention, utilising a conventional needle and an adaptor.
Figure 2C:
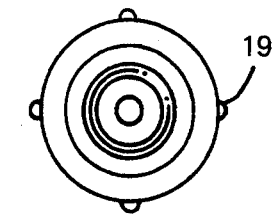
FIG. 2c is an underneath plan view of the adaptor of FIG. 1.
Figure 2A:
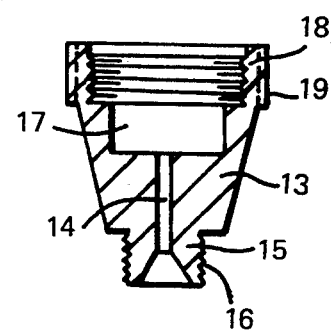
FIG. 2a is an enlarged vertical cross section of the adaptor of FIG. 1 on the line A—A in FIG. 2b.

As shown in FIGS. 1 and 2, an assembly in accordance with the invention comprises a dental syringe 1, an anaesthetic cartridge 2 and a needle assembly 3. The needle assembly comprises a cannula 4 secured in a conventional needle hub 5 which is screw-threadedly joined to an adaptor 6. The needle assembly also includes a scabbard 7 which protects the front or injection point 8 of the cannula. The rear point 9 of the cannula has pierced the rubber diaphragm 96 at the front end of the cartridge.

The front end of the barrel of the syringe 1 is open. Its forward edge is rebated and the outer surface of the rebated portion 11 is screw-threaded. Immediately behind the rebated portion, there is a small annular shoulder 12. There are open slots on both sides of the barrel of the syringe, so that the syringe is both side-loading and front loading.

As shown in more detail in FIG. 2, the adaptor 6 comprises a frustro-conical body 13 of plastics material having an axial passage 14 to receive the cannula. At its lower end, the body extends into a boss 15 which is externally screw threaded at 16. The boss has dimensions similar to the boss 205 at the front end of a conventional syringe, so that the boss can engage the internally screw-threaded recess in a conventional needle hub, which is normally used for mounting the needle onto a conventional syringe. The front lead-in to the axial passage may be tapered (as shown) to facilitate easy insertion of the rear point of the needle.

Figure 2B:
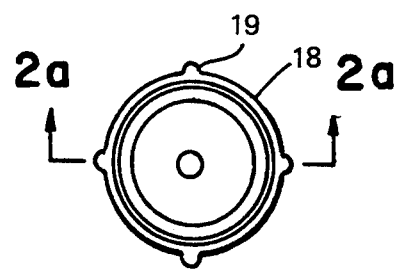
FIG. 2b is a top plan view of the adaptor of FIG. 1.

At its rear end, the body 13 has a cylindrical recess 17 for receiving the front end of the cartridge 2. The body 13 then extends further in the rearward direction to form an annular skirt 18 which is internally screw-threaded for engagement with the rebated portion 11 of the syringe. The external surface of the skirt carries a plurality of ribs 19 equiangularly spaced around the circumference and extending parallel to the axis; FIGS. 2b and 2c show four external ribs spaced at 90° apart. The external ribs 19 extend by about 0.5 mm from the external surface of the skirt which has a diameter of about 12.5 mm, and preferably the ribs are of generally round cross section with a radius of about 0.5 mm plus or minus 0.05 mm. The ribs form the portion of greatest diameter on the adaptor 6 or the needle hub 5. This feature enables the needle assembly to be removed in the removal device of the present invention, as described with reference to FIGS. 11-19 below.

In use a dentist takes the syringe 1 and screws a new adaptor 6 onto the front of the syringe. Then the dentist screws a conventional needle 3 onto the adaptor 6, so that the rear point 9 of the cannula enters the front opening of the barrel of the syringe. The dentist then inserts a cartridge into the syringe through the slot 20 in the side wall of the barrel. By pushing the cartridge forward the rubber diaphragm 96 at the front end of the cartridge is pierced by the rear point 9 of the cannula, thus allowing the anaesthetic liquid to enter into the cannula. Alternatively, the cartridge may be placed in the barrel before the needle assembly is screwed onto it, or the cartridge may be applied to the needle assembly first and may then be slid into the barrel through the front opening, after which the needle assembly is screwed into position. The point 9, where aspiration occurs, can be easily seen, which is not currently the case with front-loading syringes. It is a special advantage of the present invention that the syringe can be loaded from the front or the side at the dentist's discretion.

When the dentist is ready to administer the anaesthetic, he/she removes the scabbard 7, places the front point 8 of the cannula in a patient's jaw, and presses the plunger in the conventional manner. The front end of the cartridge 2 seats in the recess 17 in the body of the adaptor and butts against the body 13. It will be noted that the barrel of the syringe 1 is somewhat shorter than that of a conventional syringe (such as shown in FIG. 27) so that the cartridge can enter into the recess 17 in the adaptor. It is not necessary that the adaptor grips tightly around the front end of the cartridge. The cartridge fits smoothly into the adaptor socket. Frictional contact between the cannula and the rubber diaphragm in the cartridge assists in keeping the two components together.

When the dentist has completed giving the anesthetic injection, he can remove the needle assembly and the cartridge by unscrewing the adaptor 6 from the syringe barrel. Advantageously, such unscrewing is achieved by the removal device described below with reference to FIGS. 11–13. Otherwise, it can be achieved by other mechanical or gripping means, or manually. When the adaptor is unscrewed it is still attached to the needle 5 and the cartridge 2, and the whole assembly is at liberty to fall freely into a container for disposal.

In the assembly according to the invention, there is no small orifice at the front of the syringe, which eliminates the possibility of cross-infection when a new needle is pushed through an already contaminated orifice in a conventional syringe. By use of the adaptor, conventional needles and cartridges can be used.

Figure 3:
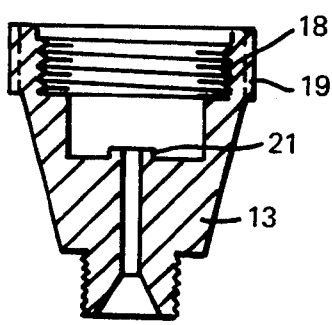

FIG. 3 shows an adaptor similar to that of FIG. 2 but it has the added feature that it incorporates a rearward protrusion 21 on the body 13 in the recess 17. This protrusion enables a front aspiration effect to be achieved by moving the cartridge forwardly against the protrusion 21. Such movement of the cartridge may be achieved by a lever or the like on the barrel of the syringe.

Figure 4:
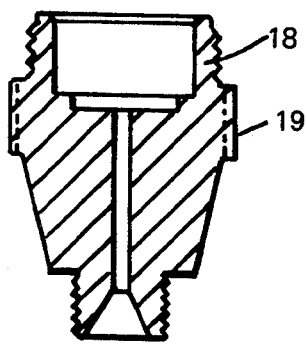
FIG. 4 shows a further alternative adaptor similar to that of FIG. 2a but having external screw-threads for engagement inside the barrel of a syringe.

FIG. 4 shows an adaptor similar to that of FIGS. 2 and 3 but the skirt 18 is integrated into the body portion surrounding the recess 17 and this portion is externally screw-threaded for engagement with an alternative syringe whose barrel is internally rebated at the lower end, with internal screw threads on the rebated portion.

In the embodiment of FIG. 4, the ribs 19 for engagement with the removal device are arranged around the body 13 and form the portion of it which is of greatest diameter. The embodiment of FIG. 4 can also be provided with the front aspiration protuberance 21 of FIG. 3.

As shown in FIGS. 5 and 6, alternative embodiments of the invention have many features which are similar to those of FIGS. 1 and 2, and the same reference numerals are used for corresponding features.

In the embodiment of FIGS. 5a and 6a, the syringe is the same as that shown in FIGS. 1 and 2, but the needle hub and adaptor have been incorporated into a single unit. In this embodiment, the hub 25 comprises an integral body which includes a conical front portion, in which the cannula is secured and which at its rearward end defines a location recess 17 for the cartridge; the body extends rearwardly to form an annular skirt 18 which is internally screw-threaded for engagement with the rebated portion 11 at the lower end of the syringe. The external surface of the skirt 18 carries ribs in the same manner as described for the embodiment of FIGS. 1 and 2.

The scabbard 26 flares rearwardly so that it can surround the skirt 18 of the needle hub and extend for a short distance rearwardly thereof and rearwardly of the rear point 9 of the needle.

As shown in FIG. 6a, a cap 28 is also provided for protecting the rear point of the needle prior to use. The front rim of the cap is a push-fit within the rear rim of the scabbard. Because of the rearward extension of the scabbard, there is virtually no risk of the dentist getting a needle-stick injury from the rear point 9 of the needle even after the cap 28 has been removed.

In using this embodiment, the dentist removes the cap 28 and screws the needle assembly onto the end of the syringe with the aid of the scabbard which has internal ribs to engage with the ribs 19 on the needle assembly and external ribs 27 to facilitate gripping by a dentist's fingers. The shape of the scabbard makes attachment of the needle to the syringe easy and not a strain on the eyes. Because of the internal ribs, the scabbard acts as a tool for applying torque. When the needle/scabbard assembly is screwed fully onto the syringe, the dentist loads the cartridge 2 into the syringe as described previously. Alternatively the cartridge may be inserted into the syringe, and the needle assembly may be screwed onto the syringe, with the needle piercing the diaphragm at the front end of the cartridge. After the injection, the dentist can remove the needle assembly and cartridge together by use of the removal device of FIGS. 11–13, as already described. Due to the open slots on both sides of the syringe barrel, the dentist can help the cartridge out of the syringe, if necessary.

This embodiment also has the advantage that there is no small orifice at the front end of the syringe. Furthermore, in this embodiment it is not necessary to assemble the adaptor and the needle hub, as required for the embodiment of FIGS. 1 and 2, so that the dentist has one less component to handle.

FIGS. 5b and 6b show an alternative embodiment of a needle assembly similar to that of FIGS. 5a–6a except that the hub body does not have a recess 17 specially configured to receive the front end of the cartridge 2. Instead the syringe 1a is longer than that of FIG. 5a, so that the cartridge 2 lies wholly within the syringe. Thus the front end of the cartridge (together with the front end of syringe) is accommodated within the recess 83 defined by the skirt 18. When the assembly is being removed from the syringe, frictional contact between the needle and the cartridge diaphragm is sufficient to cause the cartridge to drop out of the syringe with the needle assembly.

The scabbard 7 flares rearwardly to form a ring portion 95 which surrounds the skirt 18 of the needle hub. The ring portion 95 is internally configured to mate with the ribs 19 on the skirt 18. The scabbard 7 extends rearwardly of the rear edge of the skirt 18 and its rear rim further extends rearwardly of the rear point 9 of the needle.

As shown in FIG. 6b, a cap 28 is also provided for protecting the rear point 9 of the needle prior to use. The front rim of the cap is a push-fit within the rear rim of the scabbard. The inside wall of the rear rim of the scabbard tapers slightly and the front rim of the cap has a corresponding taper. This facilitates the cap 28 being pushed off by the operator's thumb while the scabbard is held in the palm of the same hand. As the needle point 9 does not project rearwardly of the rear rim of the scabbard, there is little danger of the needle being bent or of the operator's thumb being pierced by the needle during removal of the cap.

Furthermore as the needle point 9 is shielded within the scabbard, there is little danger of the operator piercing his/her finger during the period between removal of the protective cap and installation of the needle assembly into a syringe. Nevertheless because the needle point 9 projects rearwardly of the skirt 18, it will be seen from FIG. 5b that after installation onto a syringe the rear point 9 of the needle extends far enough into the cartridge to be visible at the point of aspiration. This is an advantage over the arrangement shown in GB 1,383,905 Amalgamated Dental Company Limited in which the rear point of the needle is shielded within the cylindrical skirt of the needle holder, with the result that the point of aspiration is hidden from view in the needle/syringe assembly. It is important for the operator to be able to see the point of aspiration. Therefore the provision of a needle-point shield by the scabbard (which is removed before use of the assembly) rather than by the needle hub is a definite advantage.

If a patient requires more than one dose of anaesthetic e.g. when a wisdom tooth is to be removed, the operator may want to remove an empty cartridge from the syringe and insert a fresh one without disturbing the needle. This can be achieved by removing the cartridge through one of the slots in the side of the syringe barrel and inserting a fresh cartridge by the same route. With the assembly of GB 1,383,905 Amalgamated Dental Company Limited such an exchange of cartridges would be difficult because the front end of the cartridge is held firmly in place by the skirt of the needle hub (see page 3 line 89). In the device of the present Application, the front end of the cartridge 2 (together with the front end of the syringe 1) is accommodated within the recess 83 but may be freely withdrawn from it. After use, frictional contact between the needle 4 and the cartridge diaphragm 96 is sufficient to cause the cartridge to drop out of the syringe when the needle assembly is being removed.

The rear rim of the scabbard 7 acts as a guide for the syringe when the components are being assembled together, the rear rim having an internal diameter only slightly greater than the external diameter of annular shoulder 12 on the syringe barrel above the rebated portion 11.

The embodiment of FIGS. 5b and 6b has the added feature that a plurality of ribs 97 are provided on the external surface of the ring portion 95 of the scabbard. The ribs 97 form the portion of greatest diameter of the scabbard. The ribs 95 are spaced around the circumference and extend parallel to the axis. Suitably there are four ribs spaced at 90° apart.

This feature enables the needle assembly having the scabbard in situ to be removed by a removal device of the kind illustrated in FIGS. 11-19 below. A special removal head 51 may be provided with the removal device, the removal head having a sufficiently large internal diameter to receive the ring portion 95 of the scabbard and being internally configured to engage with the ribs 97.

Thus, if desired, a dentist may re-apply the scabbard onto the needle assembly after use. Due to the wide mouth of the scabbard at its rear rim, there is less risk of needle-stick injury occurring than with a conventional scabbard. The dentist may then leave the assembly for later removal of the needle, scabbard and cartridge by means of the removal device, or the dentist may hand the assembly to an assistant who can take it to the removal device with the scabbard on it.

If desired, manual twisting can safely be applied to the scabbard, so that the needle, scabbard and cartridge are removed from the syringe without use of the removal device of FIGS. 11-19.

Figure 7:
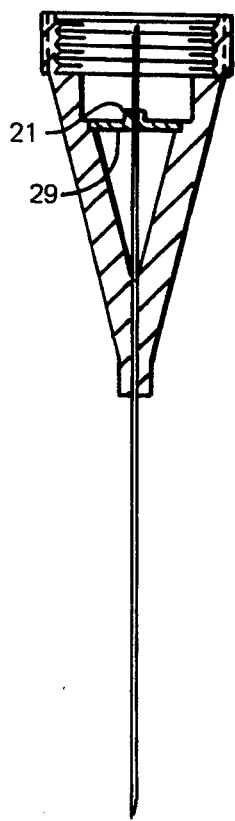
FIG. 7 is a vertical cross section of an alternative embodiment of the needle similar to FIG. 6 but omitting the scabbard and protective cap.

FIG. 7 shows a needle similar to that of FIG. 6 but having an insert disc 29 which assists in locating the cannula and also carries a protrusion 21 for achieving a front aspiration effect, as in the embodiment of FIG. 3.

Figure 8:
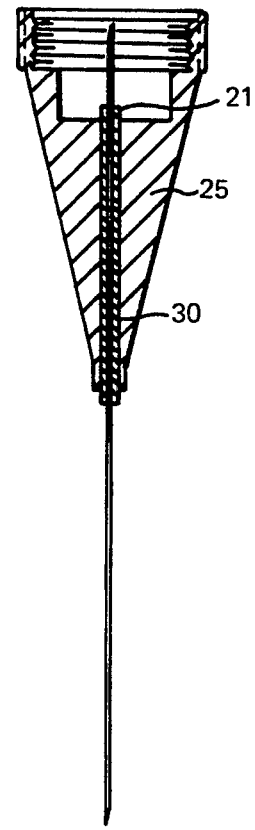
FIG. 8 is a view similar to FIG. 7 of a further alternative embodiment of the needle.

FIG. 8 shows a further needle similar to that of FIG. 6 but with a tubular insert 30 placed between the cannula and the body 25 of the hub so as to support the full length of the cannula. The rear end of the insert 30 also forms a protrusion 21 for achieving the front aspiration effect.

FIGS. 7 and 8 show a method of significantly reducing the problem of moulding a long narrow hole to support the cannula. The inserts 29 and 30 make the moulding easier.

Other possible variations in the form of the needle hub will be apparent to those skilled in the art.

Figure 9:
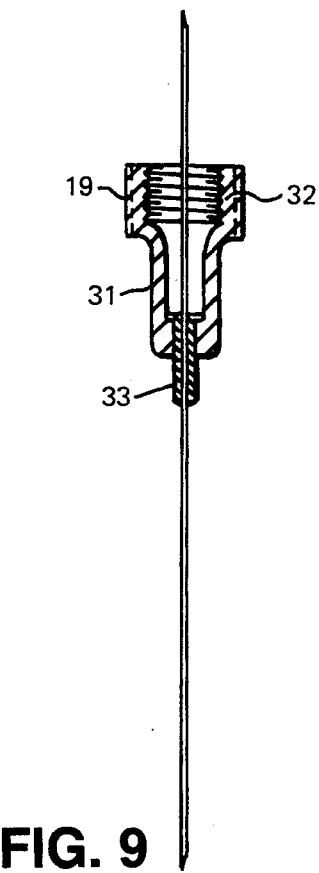
FIG. 9 is a vertical cross section of a further embodiment of a needle for use with a conventional syringe on the line B—B in FIG. 10.

FIG. 9 shows another alternative embodiment of the invention, which is suitable for use with a conventional syringe. The needle hub has a body 31 whose rear portion 32 is internally screw-threaded for attachment to the front end of a conventional syringe. The outer surface of the portion 32 carries ribs 19 similar to those described with reference to the embodiment of FIGS. 1 and 2. The ribs form the portion of greatest diameter. The body does not have a rear shoulder of greater diameter, as is present in conventional needle assemblies.

The embodiment shown in FIG. 9 has a tubular insert 33 to assist in locating the cannula in the body. However the cannula could also be mounted in the body by moulding it in position or by use of adhesives.

Figure 10:
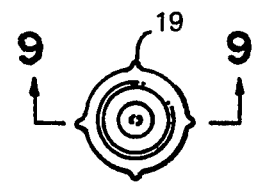
FIG. 10 is a plan view of the needle of FIG. 9.

FIG. 10 shows a plan view of the embodiment of FIG. 9, and the ribs 19 can be clearly seen. This needle assembly can be removed from the syringe after use by a removal device similar to that described below with reference to FIGS. 11-19 but with a removal head of smaller diameter than that which is used for removing the needle assemblies of FIGS. 1-8. However with this embodiment the cartridge must be removed separately from the syringe in the conventional manner; the cartridge should be removed first, before unscrewing the needle head, otherwise the frictional grip between the cannula and the rubber diaphragm of the cartridge could inhibit the needle from falling by gravity into the container.

Figure 11:
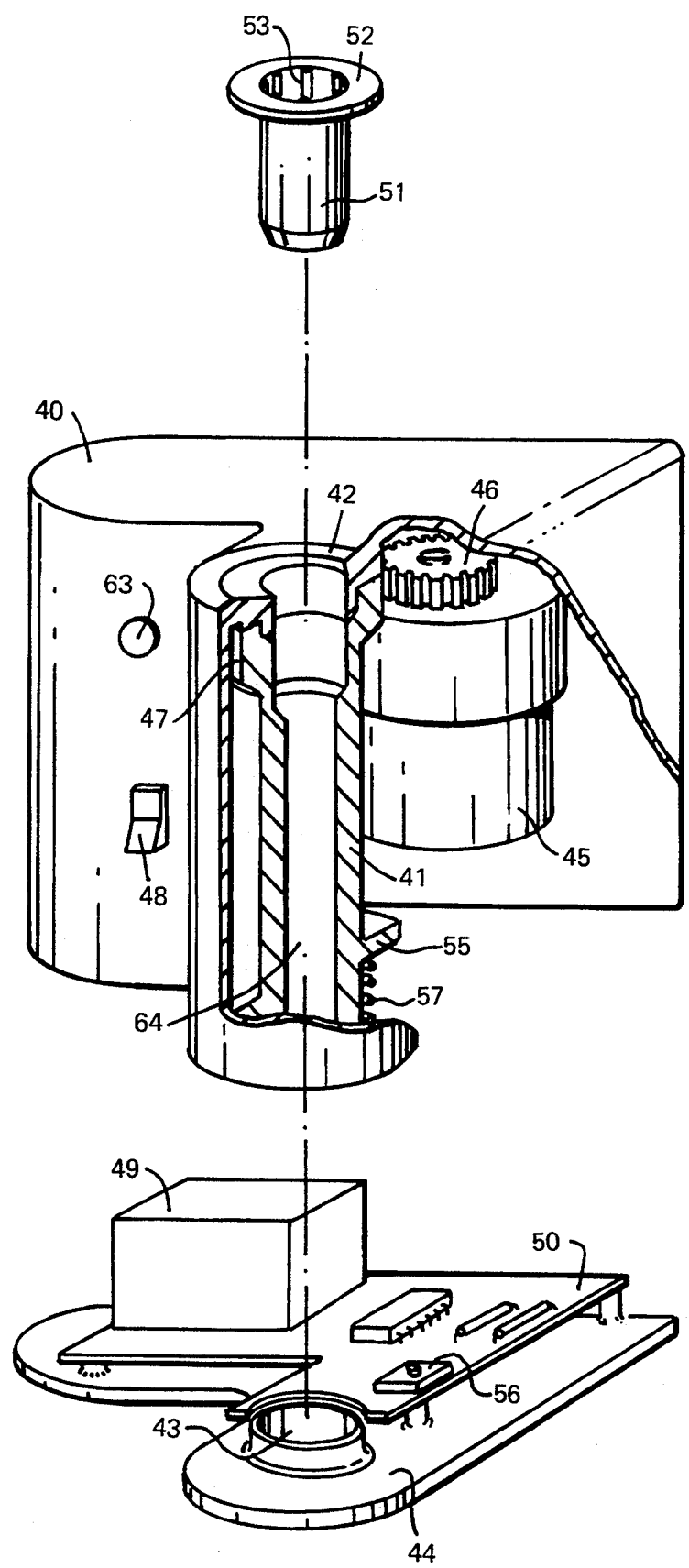
FIG. 11 is an exploded projection of one embodiment of a device in accordance with the invention for removing a needle from a syringe.

FIGS. 11-13 show one embodiment of a removal device in accordance with the invention. The device comprises a housing 40 in which is mounted a hollow shaft 41 which is rotatable about a vertical axis. The shaft is mounted at the upper end on a bushing 42 which is moulded onto the housing 40 and which fits into the inside of the shaft. At the lower end, the shaft fits into a bushing 43 which is mounted onto a baseplate 44, which forms the base of the housing 40 and fits up inside the housing.

The shaft 41 is rotated by an electric motor 45 through a gear 46 which meshes with a gear formation 47 on the external surface of the shaft. The input power to the motor is controlled by a switch 48 on the housing and passes through a transformer 49 and a control board 50 (preferably a printed circuit board) on the baseplate. The transformer for power supply can be external, if desired, either plug-mounted or as a separate unit which will ensure that only low voltage goes to the removal device. The power that is supplied to the control board powers the various components thereon. A light indicator 63 is provided on the housing to show when the power supply is "on".

A removal head 51 is insertable into the top of the shaft so as to engage with the internal surface of a rebated portion thereof, either as a friction fit or by mating shapes such as octagonal surfaces on the exterior of the removal head and the interior of the rebated top portion of the shaft, or one or more splines on the removal head mating with a groove or grooves in the shaft. A clear passage 64 is present through the removal head 51 and the shaft 41. The removal head 51 is a hollow cylinder with a top flange 52. The internal surface of the removal head carries a series of ribs 53 (for example 8 ribs) which extend parallel to the axis. As shown in FIG. 12, these ribs 53 are intended to engage with butting surfaces against the ribs 19 on the external surface of a needle assembly. However the ribs 53 are spaced sufficiently far apart around the internal circumference of the removal head 51 that a needle assembly can be inserted therein and can drop therethrough without impediment.

Toward the lower end thereof, the shaft 41 carries a horizontal flange 55 which operates a micro-switch 56 carried on the baseplate. The shaft is urged upwardly by a helical spring 57 which acts between the flange 55 and the baseplate.

As shown in FIG. 13, a "sharps" container 58 is mountable below the baseplate 44 by a sliding engagement on horizontal track 59. The sharps container 58 is deep enough to receive a needle assembly and cartridge vertically. The bushing 43 on the baseplate 44 has a central opening which communicates with the sharps container 58.

The container 58 has a top wall and a cover 60, as shown in FIG. 14. The top wall has an aperture 61 (shown in dotted outline in FIG. 14) while the cover 60 has an aperture 62. When the container is in use, the cover 60 is rotated relative to the container so that the holes 61 and 62 are aligned with each other and are aligned also with the opening through the bushing 43. After the container has been filled with needle assembly and cartridges, the container can be slid horizontally away from under the baseplate 44, and the cover 60 can then be rotated relative to the container so that the apertures 61 and 62 are no longer in alignment and the container is thus sealed. This arrangement has the advantage that a separate cover does not have to be stored while the container is being filled. The cover can be such that when it is rotated it clicks into place which makes removal difficult. Alternatively the cover can operate as a sliding shutter which can be slid to-and-fro by finger pressure and can click into closed position.

In an alternative embodiment, a container can be located loosely underneath the baseplate, either being held by hand or mounted on a suitable surface.

In normal use, the removal head 51 is kept in position at the top of the shaft 41. When a dentist has completed the administration of an anesthetic, he/she inserts the needle assembly downwardly into the removal head until the shoulder 12 on the front end of the syringe (FIGS. 1 and 2, 5 and 6) or the front end of the syringe itself in the case of the embodiment of FIGS. 9 and 10, abuts against the top of the ribs 53 or the flange 52 on the removal head 51. The dentist switches on the power switch 48 and then applies pressure on the syringe 1, in a downward direction. This has the effect of moving the shaft 41 downwardly for a few millimeters which causes the flange 55 to operate the micro-switch 56. The annular shape of the flange 55 ensures that the microswitch is always activated regardless of where the shaft has stopped after its previous rotation. Once the microswitch 56 has been activated, the dentist releases the downward pressure and the spring 57 returns the shaft 41 upward to its original position. The micro-switch activates the motor 45, which causes the shaft 41 and the removal head 51 to rotate. The ribs 53 on the removal head engage against the ribs 19 on the needle assembly. The direction of rotation (as shown in FIG. 12) is such as to unscrew the needle assembly from the syringe. The machine can be activated and operated by one hand.

When the needle assembly has been unscrewed from the syringe, the motor is switched off. The rotation of the shaft can be stopped after a fixed number of revolutions by providing a sensing device such as an optoelectric sensor mounted on the control board 50 which detects the number of revolutions. The needle assembly, with the cartridge 2 attached to it, then falls freely in a vertical direction through the shaft 41 and the bushing 43 into the container 58.

The cartridge 2 passes through the shaft 41 in an unbroken condition. If rotatable gripping means such as those of U.S. Pat. No. 4,798,587 Willoughby were used for removing a needle/cartridge assembly, there would be a serious risk of a cartridge being fractured and the fragments of glass being caught in mechanical parts of the device.

It is possible to incorporate a time delay device into the electrical circuit activated by the micro-switch, so that a period of a few seconds elapses between the time when the shaft is pushed downwardly and the motor starts up to rotate the shaft. This allows the dentist sufficient time to relax the downward pressure on the syringe and to re-grip it in a suitable manner to counteract the rotation action of the removal head, which is necessary to unscrew the needle assembly from the syringe.

In an alternative embodiment, the activation of the motor by downward pressure on the shaft 41 can be replaced by the use of a switch similar to that shown at 48 in FIG. 11.

The housing 40 is preferably moulded of plastics material in such a way that there are no joints on the external surface, preferably by moulding the housing all in one piece. This has the advantage that it does not allow the ingress of water which is used for cleaning or sterilisation procedures or which may be splashed onto the housing, as may be expected to occur in a dental surgery. The switch 48 and light indicator 63 are mounted in such a manner that water will not enter through or around them.

The potentially-contaminated needle assembly and cartridge falling through the shaft 41 do not contact any of the mechanical workings of the device, so that there is no risk of contamination being transferred to them.

A safety device can be incorporated into the electrical circuit so that the shaft 41 will not be rotated if there is no container 58 in position beneath it. A counting device can also be added, for the purpose of counting the number of needle assembly and cartridge units which has passed into a single container, so that a warning (such as a light or sound bleeper) can be operated to indicate that the container is almost full. The counter could be set to zero each time a new container 58 is fitted.

It should be noted that the shaft 41, when in its rest position, has its bottom edge flush with the underneath surface of the base plate 44. The holes 61 and 62 in the top wall and cover of the "sharps" container 58 are large enough to accommodate the lower part of the shaft 41. Thus when the holes 61 and 62 are aligned with each other and with the opening through the bushing 43, the shaft 41 can be pushed downwardly to activate the microswitch. However if the container 58 is closed because the holes 61 and 62 are not in alignment, the shaft 41 cannot be pushed down and so the removal device can not be operated. This is an added safety feature.

The removal head 51 can be removed for regular cleaning and sterilisation. The shaft is fitted into the device in such a way that water can be poured through it with no risk of the water getting into the electrical or other internal workings of the unit. The shaft 41 can be integrally moulded of plastics material. As the top bushing arrangement fits inside the top edge of the shaft, and the bottom bushing arrangement is outside the shaft, there is a clear passage for water to flow through without any gaps or joints into which the water can enter. The baseplate 44 fits up inside the main housing in such a manner that run-off water from the housing will not enter the inside of the machine.

Alternatively, the shaft 41 can be designed in such a way that it can be completely removable for cleaning, if desired.

A removal head of smaller internal diameter but similar configuration may also be provided for unscrewing the needle assembly of FIGS. 9 and 10. This removal head may have the same external dimensions as removal head 51, so that it may be fitted into the same shaft 41. Alternatively a device having a shaft of smaller internal diameter may be provided.

Figure 15:
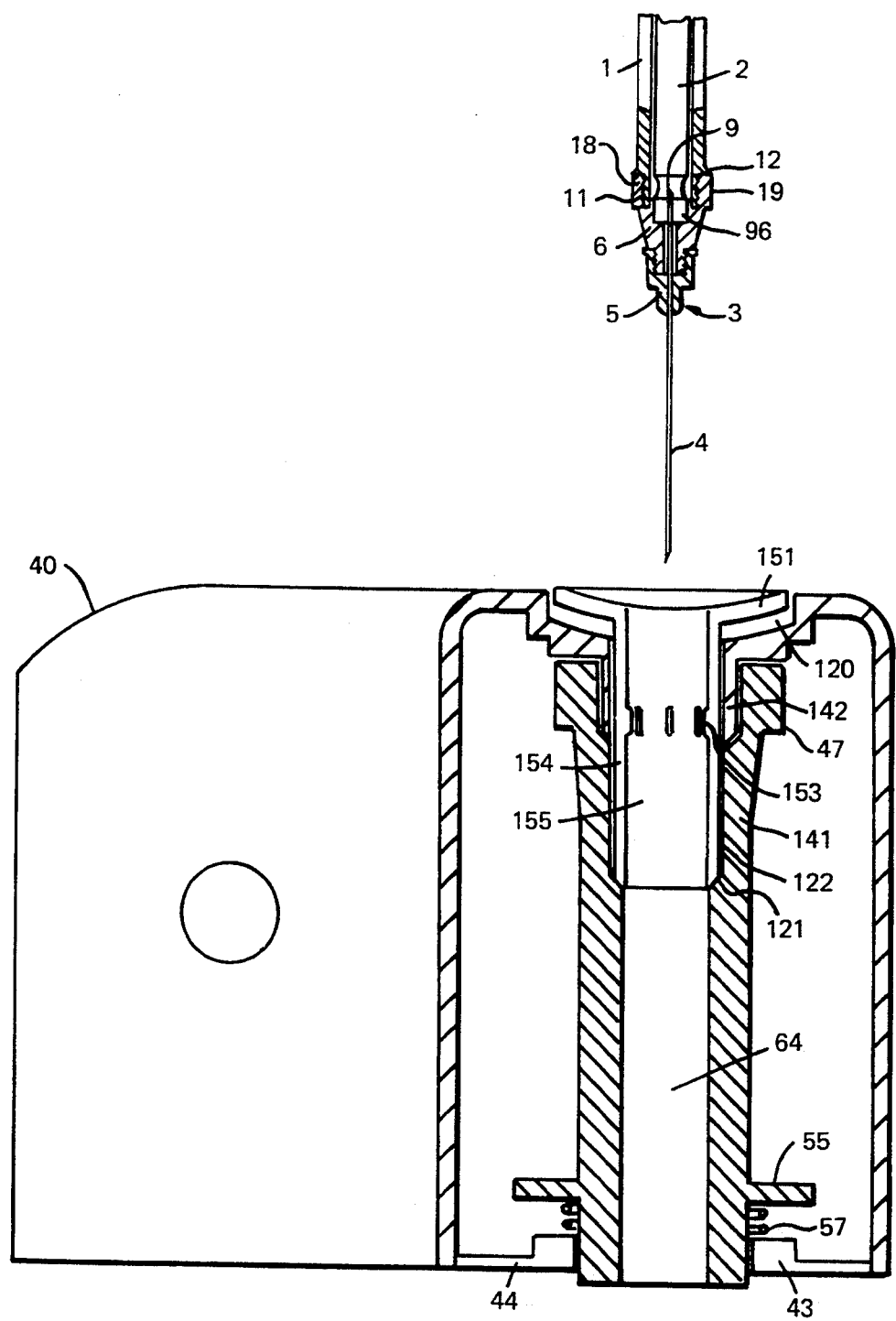
FIG. 15 is a vertical cross section through the central shaft of a slightly modified embodiment of a removal device, with a fragment of the needle/syringe assembly of FIG. 1 positioned for entry into it.
Figure 16:
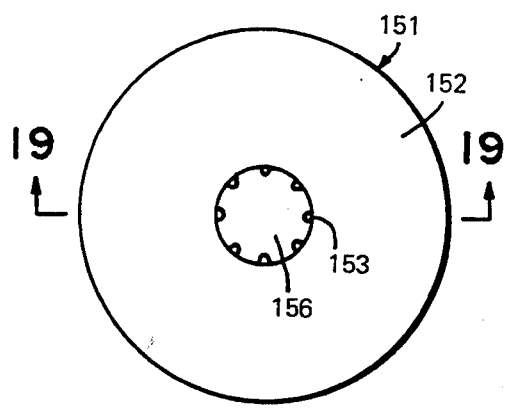
FIG. 16 is a top plan view of a removal head.
Figure 17:
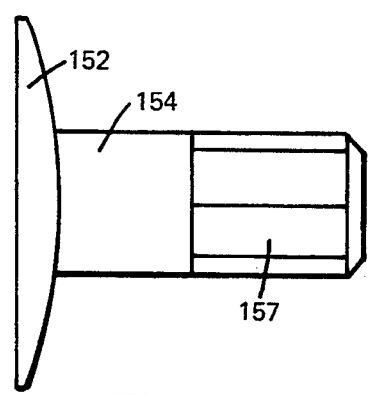
FIG. 17 is an elevation of the removal head of FIG. 16.
Figure 18:
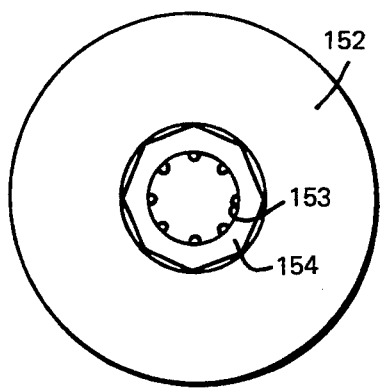
FIG. 18 is an underneath plan view of the removal head of FIG. 16.
Figure 19:
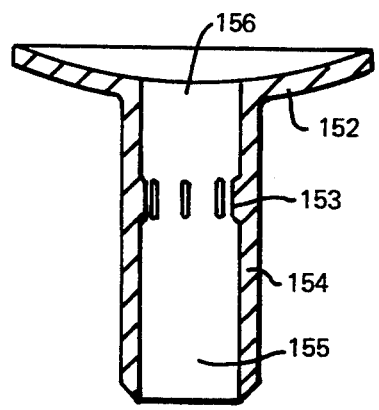
FIG. 19 is a vertical cross section of the removal head of FIG. 16 on the line C—C in FIG. 16.
Figure 20:
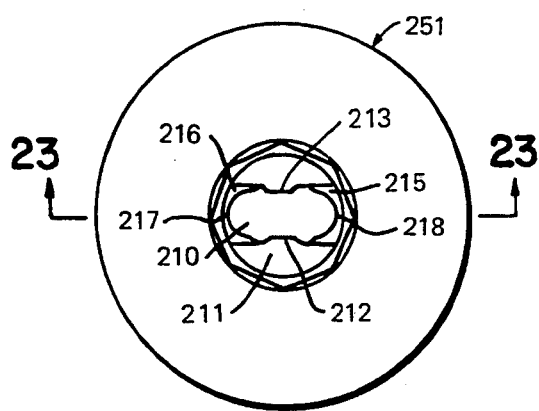
FIG. 20 is an underneath plan view of an auxiliary removal head for use with conventional needle assemblies.

FIG. 15 is a vertical cross section through a preferred embodiment of the removal device which is a variant of that shown in FIG. 11. Similar numerals are used for similar parts. For clarity the electric motor 45 and drive wheel 46 are omitted, as are other electrical components on the base plate 44.

A recess 120 is provided at the top of the housing 40. At the centre of the recess, the plastics material of the housing extends downwardly to form a thin walled annular bushing 142. The top of the hollow shaft 141 is rebated to accommodate this bushing 142. The shaft is rotatable relative to the top bushing 142 and the bottom bushing 43, through which the shaft 141 passes.

The shaft 141 is also rebated at 121 to receive the removal head 151 which is described in greater detail below. The shaft has an octagonal internal surface at 122 to interfit with the removal head 151. The flange at the top of the removal head fits into the recess 120 but is spaced from the bottom of the recess so that rinsing water may flow through the recess and down the space between the removal head 151 and the bushing 142 or sleeve 154, leading to the passage 64 through the shaft. The removal head is free to rotate in the bushing 142 when the shaft is rotated by drive transmitted through the gear formation 47.

FIGS. 16–19 show the preferred embodiment of the removal head. The removal head 151 comprises a broad flange 152 with a central aperture, and a sleeve 154 defining a passage 155 which is aligned with the aperture 156 in the flange. The external surface of the sleeve 154, in its lower region, has an octagonal surface 157 for interfitting with the shaft 41 of the removal device.

The internal surface of the sleeve is provided with a series of ribs 153 extending parallel to the axis of the sleeve and protruding into the passage 155. The ribs are spaced about 10 mm down the sleeve from the aperture 156. As shown in the drawings, there are 8 ribs spaced equiangularly around the sleeve, each rib being of approximately semicircular cross section with a radius of about 0.5 mm.

The passage 155 has a diameter marginally greater than the diameter of the shoulder 12 at the front end of the syringe, so that the shoulder is a sliding fit in the passage. The radially-inward surfaces of the ribs define a notional circle which is smaller in diameter than the shoulder 12 but greater in diameter than the cylindrical surface from which the ribs 19 of the needle adaptor or needle hub protrude (as shown diagrammatically in FIG. 12).

When a needle/syringe assembly is inserted into the removal head as shown in FIG. 15, the front end of the syringe enters the passage 155 until the shoulder 12 buts against the top of the ribs 153. Further downward pressure on the syringe actuates the removal device to unscrew the needle from the syringe. The operation of the removal device is the same as described above for FIGS. 11–14.

FIGS. 20–23 show a preferred embodiment of an auxiliary removal head for unscrewing conventional needle assemblies, such as shown in FIGS. 27–29.

The removal head 251 is similar to the removal head 51 but it does not have internal ribs 53. Instead it has a specially configured slot 210 (resembling a double headed keyhole) in the top plate of the removal head, the slot having with two substantially round end regions separated by a narrow portion which is defined by a pair of shoulders 211 terminating in opposed engagement surfaces 212, 213 and which is located on the axis of the removal head. The round end regions (which are only-partly defined by arcuate shelf portions 215, 216 and form the wide part of the double keyhole shape) have a diameter greater than that of the annular shoulder 208 on a conventional needle hub, while the separation between the engagement surfaces 212, 213 is equal to the diameter of the needle hub at its gripping surface 207. The size and configuration of the hole 210 can of course be varied to accommodate other sizes and shapes of needle assembly.

The arcuate shelf portions 215, 216 have lower surfaces which are inclined downwardly towards the ends 218, 217 of the hole. The shelf portions are above the shoulders 211.

The removal head is used in conjunction with the removal machine as described above.

When the dentist requires to remove a conventional needle (FIGS. 27–29) from the end of a syringe, he places the syringe and needle assembly in the removal head. The end of the syringe is located in the hole 210 in the removal head.

The front face of the annular shoulder 208 of the needle hub rests on the shoulder 211 of the removal head. The gripping surface 207 of the needle is located and held between the faces 212 and 213 of the removal head, so that the needle hub is engaged in the narrow part of the slot with the needle lying on the axis of the removal head.

When the syringe is pushed downwards, it activates the removal machine. Rotation of the removal head by the shaft 41 unscrews the needle from the end of the syringe. As a result of this unscrewing action the syringe moves vertically upwards all the time, being guided by the hole 210, during which time the annular shoulder 208 of the needle hub is still resting on the shoulder 211 of the removal head and the gripping surface 207 is held between 212 and 213.

When the machine stops rotating after a pre-determined number of revolutions, the syringe is pushed in a horizontal manner in either the direction of X1 or X2 (FIG. 22) while maintaining the axis of the syringe in a vertical direction. This movement of the syringe also causes the annular shoulder 208 of the needle hub to slide over the surface 211. As the annular shoulder 208 slides over the surface 211, it is forced downwards by either the wedge 215 or 216, depending on whether it is moved in the X1 or X2 direction.

The downward movement has the effect of stripping the cannula 203 from the cartridge rubber diaphragm as the syringe is moved fully over until its threaded section 205 comes in contact with either point 217 or 218 of the removal head. The needle can now fall freely by gravity into a sharps container as the annular shoulder 208 is now unobstructed by either point 212 or 213.

Figure 21:
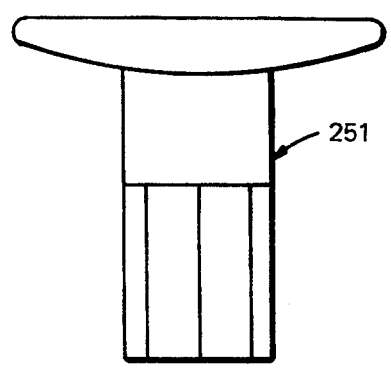
FIG. 21 is an elevation of the removal head of FIG. 20.
Figure 22:
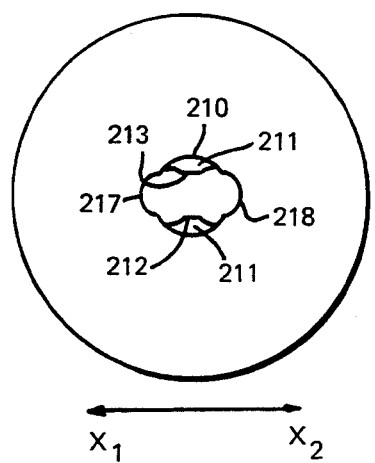
FIG. 22 is a top plan view of the removal head of FIG. 20.
Figure 23:
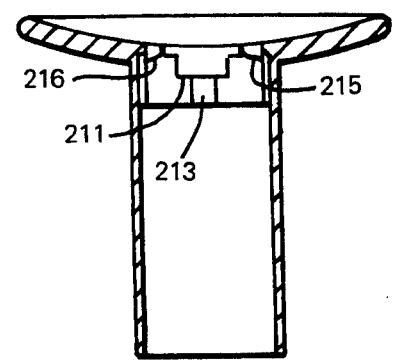
FIG. 23 is a vertical cross section of the removal head of FIG. 20 on the line D—D in FIG. 20.

As shown in FIG. 21, the removal head 251 has an octagonal lower portion on its external surface to inter-fit with a corresponding portion on the central shaft of the removal device.

In an alternative embodiment, the removal head can be designed to allow it to be affixed to the central shaft of the removal machine by either a friction fit or a click-in effect, or splines on the removal head co-operating with grooves on the shaft.

Figure 24:
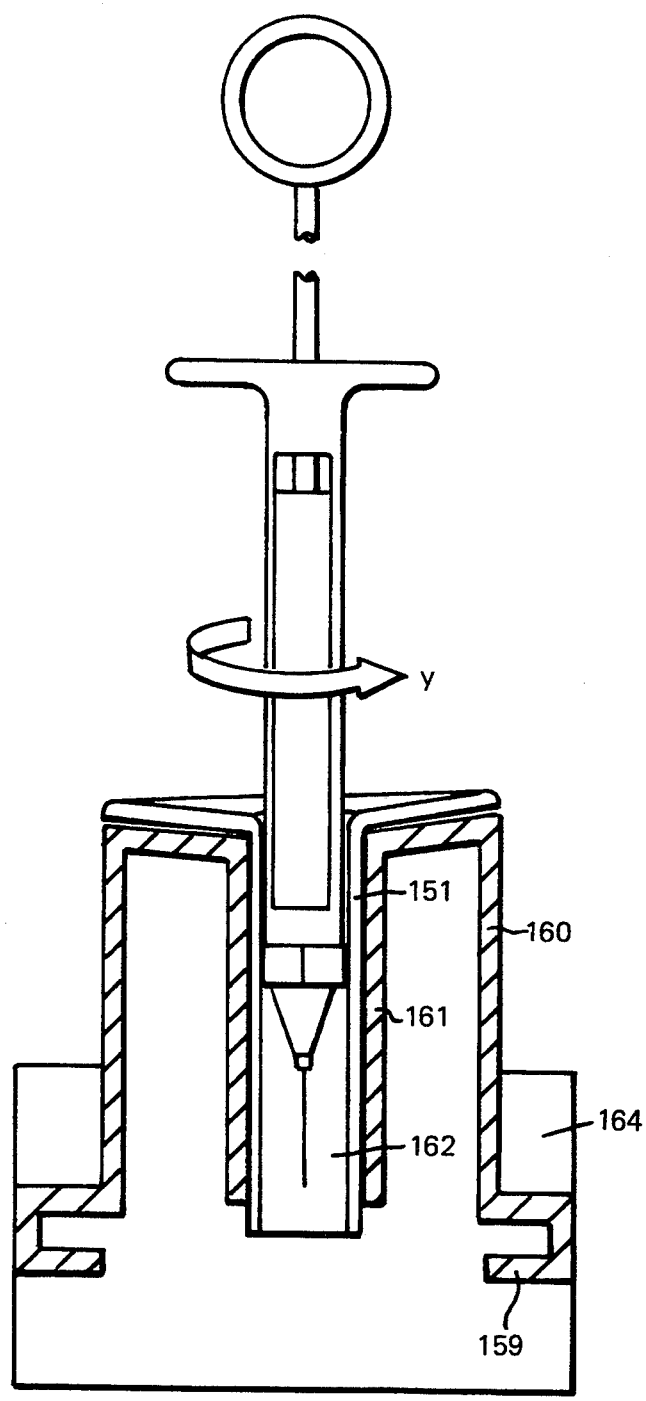
FIG. 24 is a vertical cross section of a manually-operated removal device, on the centre line thereof.

FIG. 24 shows a manual removal device utilising a removal head similar to the removal head 151. The manual removal device comprises a cylindrical hollow body 160 having a central shaft portion 161 which is open at the top and the bottom. The removal head 151 fits into the central shaft portion 161 and is held therein by the octagonal shape interfitting with a corresponding formation on the inner surface of the shaft. Alternatively the removal head may have splines which fit into grooves in the inner surface of the shaft, or the removal head may be a frictional fit into the shaft.

The body 160 is open downwardly and it has a pair of opposed channel portions 159 to receive the lip of a sharps container similar to container 58. The body also has a vertical mounting plate 164 by which it can be fixed to a wall, stand or the like.

In use, a needle/syringe assembly is inserted into the removal head 151 as described above with reference to FIGS. 16–19. The syringe is then rotated manually relative to the removal head in the direction indicated by the arrow Y. The ribs 19 on the needle adaptor or hub mesh with the ribs 153 on the removal head and rotation of the syringe therefore unscrews it from the needle. After separation of the syringe, the needle assembly and the cartridge fall freely through the passage 162 into the sharps container (not shown) below the removal device.

Alternatively the manual removal device of FIG. 24 may be used with the removal head 251 of FIGS. 20–23.

Figure 25:
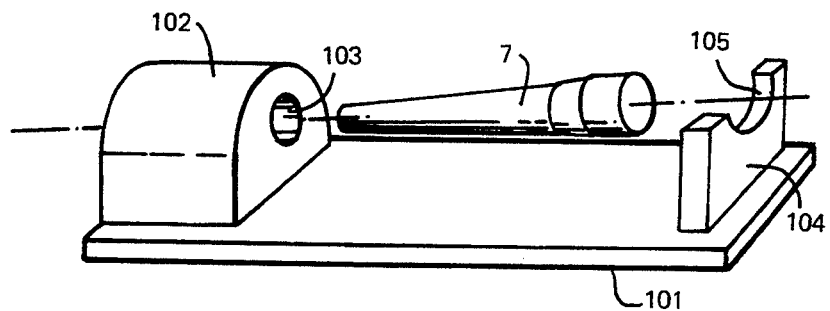
FIG. 25 is a projection of a stand showing a scabbard in line with the scabbard holder.
Figure 26:
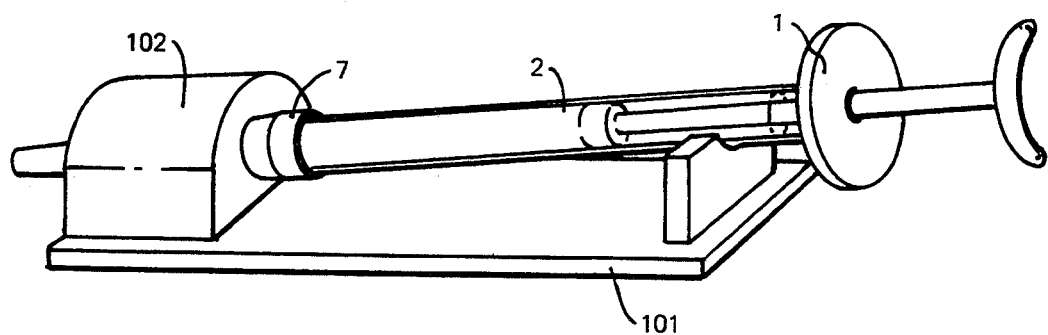
FIG. 26 is a projection similar to FIG. 25, showing a needle syringe assembly in position on the stand.

FIGS. 25 and 26 show a stand for use with a needle/syringe assembly according to the invention. The stand comprises a base 101 with a holder 102 for a scabbard 7 at one end of the base. The holder 102 is penetrated by a tapering hole 103 to receive the scabbard. The axis of the hole is at a small angle to the plane of the base 101.

At the other end of the base there is a wall 104 provided with a notch 105 defining a rest for a syringe 1.

When the needle/syringe assembly is ready for use, the operator removes the scabbard 7 from the assembly and inserts it into the holder 102. After the injection has been administered, the operator inserts the front needle point 8 into the scabbard, still in the holder, and re-applies the scabbard to the assembly without any risk of needle-stick injury. The assembly may then be left in the resting position shown in FIG. 4 until it is taken to the removal device or it is reused for administering a second injection to the same patient using a fresh cartridge.

Alternatively the removal devices as described above can be used as a stand for the needle syringe assembly between the administration of two injections to the same patient.

In the description above, reference has been made to inter-engagement of two screw-threaded components. If desired, one of such components may be initially screw-threaded, and the other may be designed so that a screw-thread is cut therein as the two components are screwed together. Advantageously, the front end of the syringe is provided with a double-start screw-thread to facilitate the fast screwing or unscrewing of the needle assembly or adaptor.

The adaptors shown in FIGS. 2, 3 and 4 can be packaged in bubble or blister packs without the need for more expensive scabbard arrangements. Different adaptors can be provided to suit needle threads in various metric or imperial sizes.

The removal devices of the present invention can be designed to be wall-mounted, to be incorporated into dental furniture, to be carried on a stand, or to be stood on a table, trolley or the like. The power driven devices may be operated by mains electricity or by battery power.

The present invention provides a system for removal of needle assemblies, and optionally also used cartridges, with substantially reduced risk of needle-stick injuries and cross infection. Any parts of the devices which are likely to be contacted by contaminated needle assemblies and/or cartridges can be easily cleaned and there is no risk of internal contamination of the mechanism. The devices are easy to operate and provide safe and reliable means of disposing of potentially dangerous needle assemblies and cartridges. When the needle assembly and cartridge are removed as one unit, there is a chain of sterility between the needle and the cartridge.

We claim:

1. A removal device for use in combination with a hypodermic needle assembly having either (a) a needle hub on a needle attachable to a syringe, or (b) an attachment adaptor for attaching the needle assembly to a syringe, wherein the needle assembly or the attachment adaptor has an external engagement configuration thereon comprising a series of external ribs parallel to the axis of the needle assembly, said removal device for removing the needle assembly from a syringe comprising:

a hollow cylindrical sleeve having an internal surface defining a passage for permitting the needle assembly and any attachment adaptor thereon to pass freely in an axial direction through the sleeve the sleeve being disposed within a hollow shaft through which the needle assembly and adaptor can pass freely in an axial direction, an internal engagement configuration on the sleeve for engaging against the external ribs of the needle assembly on the attachment adaptor when the sleeve is rotated relative to the syringe about the axis of the sleeve, said internal engagement configuration comprising a series of internal ribs on the internal surface of the sleeve, wherein the internal ribs are aligned parallel to the axis of the sleeve, and are spaced around the internal circumference of the sleeve, the internal ribs each having a radially-inward surface, and the internal diameter of the sleeve at the radially-inward surfaces of the internal ribs is greater than the diameter of any part of the needle assembly and any attachment adaptor thereon other than the said external ribs;

and wherein drive means are provided externally of the shaft for rotating it about its axis.

2. A removal device according to claim 1, wherein the series of internal ribs on the sleeve comprises up to 8 ribs spaced around the internal circumference of the sleeve.

3. A removal device according to claim 1, wherein the hollow shaft is integrally formed so that infected fluids or washing water passing through the shaft cannot gain access to the drive means.

4. A removal device according to claim 1, wherein the internal diameter of the sleeve at the radially-inward surfaces of the internal ribs is greater than the diameter of a cartridge from the syringe but smaller than the diameter of the syringe.

* * * * *